United States Patent [19]
Ueda et al.

[11] Patent Number: 5,397,679
[45] Date of Patent: Mar. 14, 1995

[54] CYCLIC CARBONATE COMPOUNDS, METHOD FOR PRODUCING THE SAME AND POSITIVE PHOTORESIST COMPOSITION USING THE SAME

[75] Inventors: Yuji Ueda, Izumi; Naoki Takeyama, Settsu; Hiromi Ueki, Osaka; Takehiro Kusumoto, Takarazuka, all of Japan

[73] Assignee: Sumitomo Chemical Company, Limited, Osaka, Japan

[21] Appl. No.: 44,482

[22] Filed: Apr. 9, 1993

[30] Foreign Application Priority Data

Apr. 10, 1992 [JP] Japan .................................. 4-090770
Jan. 18, 1993 [JP] Japan .................................. 5-005792

[51] Int. Cl.$^6$ ..................... G03C 1/492; G03F 7/004
[52] U.S. Cl. ..................... 430/270; 430/326; 430/905; 430/909; 430/920; 430/921
[58] Field of Search ............... 430/270, 326, 905, 909, 430/920, 921

[56] References Cited

U.S. PATENT DOCUMENTS

| 5,130,225 | 7/1992 | Uetani | 430/191 |
| 5,242,734 | 8/1994 | Lazarus et al. | 430/270 |

FOREIGN PATENT DOCUMENTS

| 0388343 | 9/1990 | European Pat. Off. | |
| 541112 | 5/1993 | European Pat. Off. | 430/270 |
| 3-215862 | 9/1991 | Japan | 430/270 |
| 4-226458 | 8/1992 | Japan | 430/270 |
| 4-230754 | 8/1992 | Japan | 430/270 |
| 5-34914 | 2/1993 | Japan | 430/270 |

OTHER PUBLICATIONS

The Japan Society of Applied Physics and Related Societies, The 38th Spring Meeting, Mar. 1991, (29a-Z-C-7).
The Japan Society of Applied Physics and Related Societies, The 38th Spring Meeting, Mar. 1991, (30a-ZA-3).

*Primary Examiner*—Janis L. Dote
*Attorney, Agent, or Firm*—Birch, Stewart, Kolasch & Birch

[57] ABSTRACT

This invention provides a process for producing a cyclic carbonate compound represented by the following formula (5):

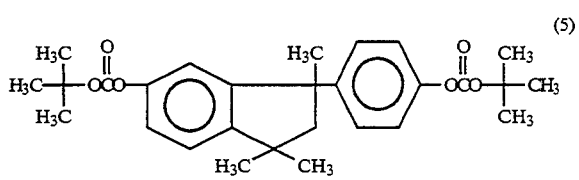

or the like which is useful as a dissolution inhibitor for use in a chemically amplified positive photoresist, as well as a positive photoresist composition comprising said cyclic carbonate compound, an alkali-soluble resin and a photo-induced acid precursor. This composition gives a positive photoresist excellent in performances such as resolution, profile, sensitivity, etc.

14 Claims, 2 Drawing Sheets

CYCLIC CARBONATE COMPOUNDS, METHOD FOR PRODUCING THE SAME AND POSITIVE PHOTORESIST COMPOSITION USING THE SAME

BACKGROUND OF THE INVENTION

1. Field of the Invention

This invention relates to cyclic carbonate compounds useful as a dissolution inhibitor for chemically amplified positive photoresists, a process for producing said compounds, and a positive photoresist composition using said compounds.

2. Related Art

Due to the recent improvement in the degree of integration of integrated circuits (64 or 256 MDRAM), it is desired that today's photoresists have an ability to form sub-micron patterns. Thus, development of a positive type photoresist suitable for use in the far ultraviolet lithography such as those using excimer laser or the like as a light source is a particularly urgent demand of the time, and a chemically amplified positive photoresist comprising an alkali-soluble resin, a dissolution inhibitor and a photo-induced acid precursor is viewed with interest. The function of this type of photoresist consists in transforming a dissolution inhibitor to a dissolution promotor by utilizing the acid generated upon exposure to light and baking, and thereby enhancing the dissolution velocity ratio between the unexposed area and exposed area of alkali-soluble soluble resin to improve the resolution. For example, the Extended Abstracts (the 38th Spring Meeting, 1991); the Japan Society of Applied Physics and Related Societies (29a-ZC-7) mentions the influence on the resolution of a chemically amplified positive photoresist composition comprising a resin prepared by partially replacing the —OH groups of polyvinylphenol with an acid removable protecting group, a dissolution inhibitor and a photo-induced acid precursor when the composition is exposed to a deep ultraviolet ray. In the paper, it is mentioned that the resin became insoluble in developing solution when the degree of replacement was elevated to 20% or above, that a ternary resist containing a dissolution inhibitor was higher than a binary resist containing no dissolution inhibitor in the dissolution velocity ratio at the time of development, and that a patterning evaluation of the ternary resist using an excimer laser stepper showed that a 0.35 $\mu$m line-and-space could be resolved (FIG. 1).

In the Extended Abstracts (the 38th Spring Meeting, 1991); the Japan Society of Applied Physics and Related Societies (30a-ZA-3), it is mentioned that a chemically amplified positive photoresist composition comprising a novolac resin, a dissolution inhibitor having t-butoxycarbonyloxy group and a nonmetallic onium salt was applied to electron beam lithography. It is also mentioned that as the onium salt of this ternary system, triphenylsulfonium triflate was undesirable but bis(t-butylphenyl)-iodonium triflate (a) exhibited an excellent property. Further, it is also mentioned that the property of this resist system varied depending on the kind of the dissolution inhibitor having t-butoxycarbonyloxy group in such a manner that polymeric t-butoxycarbonyl compounds were not good in profile (overhanging patterns) though it exhibited an excellent dissolution inhibition. It is also mentioned that, among the dissolution inhibitors of this class, [t-C$_4$H$_9$OCO—O—C$_4$H$_4$]$_2$.C(CH$_3$)$_2$ (b) was best in sensitivity and resolution. It is also mentioned that tentative resists containing the above-mentioned (a) and (b), respectively, resolved a 0.15 $\mu$m line-and-space pattern having a thickness of 0.47 $\mu$m with an exposure dose of 14 $\mu$C/cm$^2$ in electron beam lithography (FIG. 1), and that the tentative resists were useful for X ray lithography, too, and could resolve 0.2 $\mu$m contact holes in a thickness of 1.3 $\mu$m.

In Claim 1 of EP-A-0388343, there is mentioned a resist for use in photon, electron beam and X ray exposure devices comprising (A) a polymeric or molecular composition, the solubility of which is dependent upon the presence of acid removable protecting groups and (B) a polymeric or molecular composition having a sulfonic acid precursor which generates a strong acid upon exposure to such radiation. In Example 5 of the specification, for example, a resist composition for use in a 240–260 nm exposing device comprising MDT (a kind of a photo-induced acid precursor), a novolac resin and [p-t-C$_4$H$_9$OCO—O—C$_6$H$_4$)$_2$].C(CH$_3$)$_2$ (dissolution inhibitor) is mentioned.

However, the photoresist compositions mentioned above are yet unsatisfactory in resolution, profile and sensitivity.

SUMMARY OF THE INVENTION

The present inventors conducted extensive studies with the aim of providing a positive photoresist excellent in performances such as resolution, profile, sensitivity, etc. As the result, it was found that a composition containing a novel dissolution inhibitor can achieve the object.

According to this invention, there is provided a cyclic carbonate compound represented by the following general formula (I):

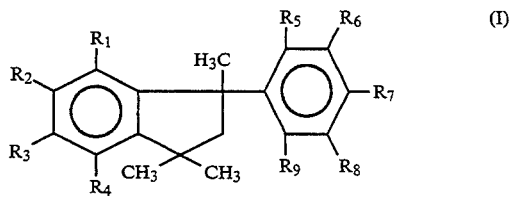

wherein R$_1$ to R$_9$ independently of one another each represent a hydrogen atom, a halogen atom, an optionally substituted straight chain or branched chain alkyl or alkenyl group, a t-butoxycarbonyloxy group or an acetyl group, provided that at least one of R$_1$ to R$_4$ is t-butoxycarbonyloxy group and at least one of R$_5$ to R$_9$ is t-butoxycarbonyloxy group; as well as a dissolution inhibitor represented by the general formula (I), a process for producing the same, and a positive photoresist composition using the same.

DETAILED DESCRIPTION OF THE INVENTION

Figure 1:
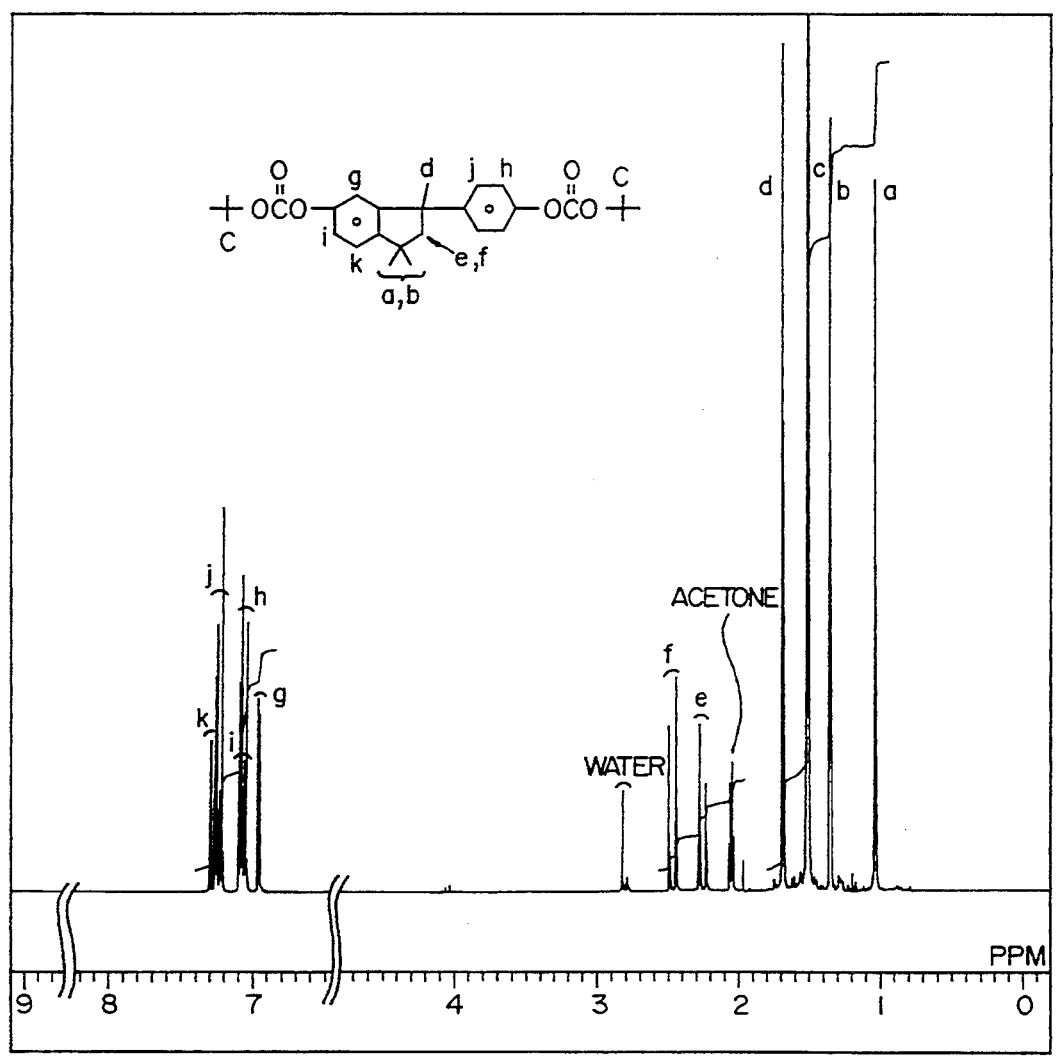
FIG. 1 is an $^1$H-NMR spectrum of to compound of Example 1.

Next, this invention will be explained below in more detail.

As the alkyl or alkenyl groups represented by R$_1$ to R$_9$, those having 5 or less carbon atoms are preferred.

As the substituent, for example, halogen atom, —OH group, —SH group, phenyl group, lower alkylthio group and the like can be referred to. As $R_1$ to $R_9$, hydrogen atom and alkyl group are preferable, and hydrogen atom, methyl group and ethyl group are more preferable.

The cyclic carbonate compound represented by the general formula (I) can be produced by reacting a compound represented by the following general formula (II):

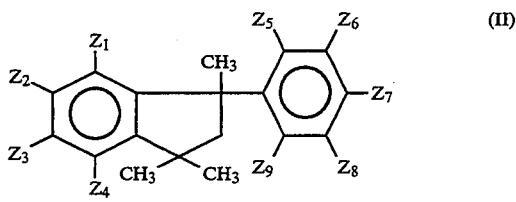

wherein $Z_1$ to $Z_9$ independently of one another each represent a hydrogen atom, a halogen atom, an optionally substituted straight chain or branched chain alkyl or alkenyl group, a —OH group or an acetyl group, provided that at least one of $Z_1$ to $Z_4$ is —OH group and at least one of $Z_5$ to $Z_9$ is —OH group, with di-t-butyl dicarbonate in the presence of a basic catalyst.

Preferable examples of the compound represented by the general formula (II) include the following:

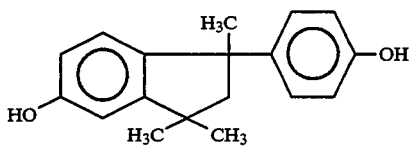
(1)

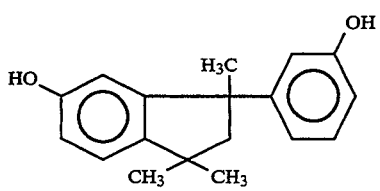
(2)

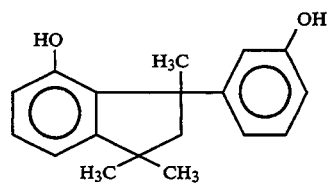
(3)

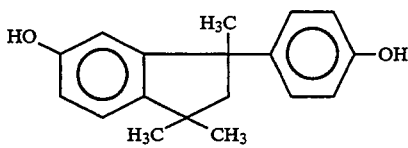
(4)

among which the compound (4) is more preferable.

The compounds represented by the general formula (II) can be produced according to the method mentioned in U.S. Pat. No. 3,288,864, etc. by using, for example, m- or p-isopropenylphenol or linear dimers thereof.

Preferable examples of the basic catalyst include alkaline substances such as sodium hydroxide, potassium carbonate and the like. These basic catalysts can be used either in the form of a solid material such as granule or powder or in the form of a solution in water or organic solvent, and preferably in the form of a solid. When used in the form of an aqueous solution, the catalyst usually has a concentration of 10–50% by weight, preferably 20–30% by weight. The basic catalyst and di-t-butyl dicarbonate are used usually in an amount of 1.1–2.2 equivalents (preferably 1.2–1.8 equivalents) and 1.0–2.0 equivalents (preferably 1.0–1.6 equivalents), respectively, both per —OH group in the compound represented by the general formula (II).

The reaction mentioned above is usually carried out in the presence of an organic solvent. Examples of the solvent include ethers such as tetrahydrofuran and the like, ketones such as acetone and the like, halogenated hydrocarbons such as chloroform and the like, and esters such as ethyl acetate and the like, among which ethers are preferable. The amount of the organic solvent is usually 1–10 parts by weight and preferably 3–6 parts by weight, per part by weight of the compound represented by the general formula (II).

In the reaction mentioned above, a phase transfer catalyst such as $(n-C_4H_9)_4NHSO_4$ or a crown ether such as 18-crown-6 and the like may be used, and the amount of the phase transfer catalyst may be decided appropriately.

The reaction temperature is usually 10°–50° C. and preferably 15°–30° C. The end point of the reaction is determined by detecting the point in time when the compound represented by the general formula (II) disappears by means of, for example, gas-, liquid- or thin layer-chromatography or the like.

The positive photoresist composition of this invention comprises a cyclic carbonate compound represented by the general formula (I) (dissolution inhibitor), an alkali-soluble resin and a photo-induced acid precursor.

Examples of the alkali-soluble resin include the resins soluble in alkali developing solution such as aqueous solution of tetramethylammonium hydroxide or the like. Preferable examples of the alkali-soluble resin include polyvinylphenol, or the novolac resins which is obtainable through a condensation of a phenol compound, including the compounds represented by the following general formula (III):

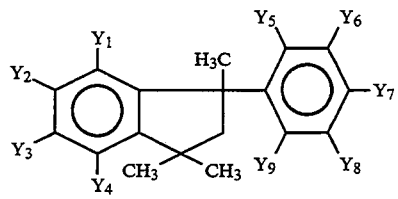

wherein $Y_1$ to $Y_9$ independently of one another each represent a hydrogen atom, a halogen atom, an optionally substituted straight chain or branched chain alkyl or alkenyl group, a —OH group or an acetyl group, provided that at least one of $Y_1$ to $Y_9$ is —OH group and at least two hydrogen atoms are attached to the o- or p-position of said —OH group, and an aldehyde such as formaldehyde or the like, in the presence of an acid catalyst such as oxalic acid, acetic acid or the like.

Preferable examples of the compound (III) can be referred a compound in which at least one of $Y_1$ to $Y_4$ is —OH group, and at least one of $Y_5$ to $Y_9$ is —OH group.

The photo-induced acid precursor is not critical, so far as it generates an acid upon exposure to radiations such as far ultraviolet ray and the like. Examples of the photo-induced acid precursor include the compounds mentioned in Japanese Patent Application KOKAI No. 62-164045, No. 63-153542, No. 53-133428, F. C. Schaefer et al. J. Org. Chem., 29, 1527 (1964), Bull. Chem. Soc. Japan, 42, 2924 (1969) and U.S. Pat. No. 3,987,037; the halogenated triazines mentioned in UK Patent No. 1,388,492; the trifluoromethanesulfonic acid esters represented by the following formulas:

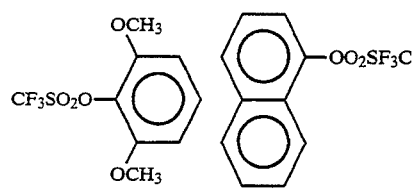

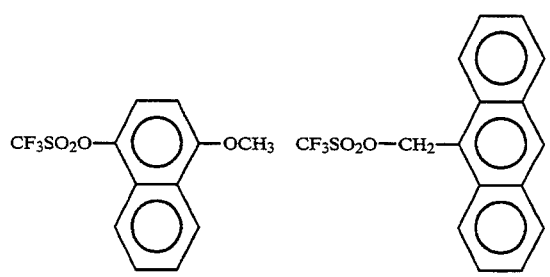

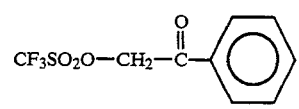

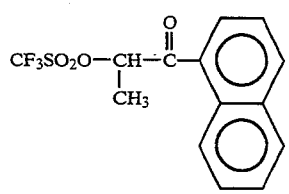

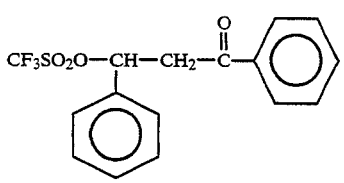

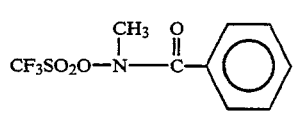

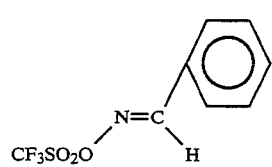

and the like; the arylsulfonylacetophenones represented by the following formulas:

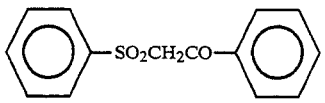

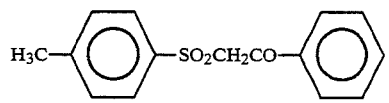

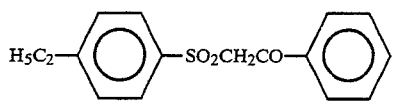

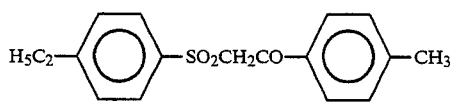

and the like; the disulfone compounds represented by the following formulas:

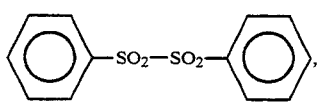

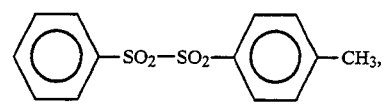

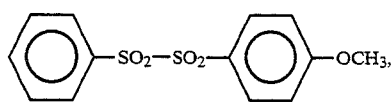

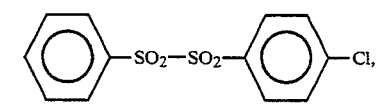

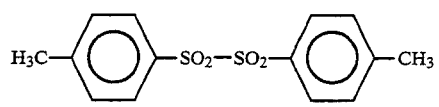

and the like; and the onium salts represented by the following formulas:

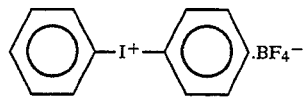

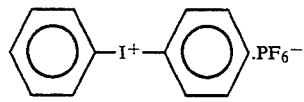

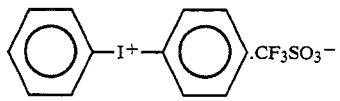

-continued

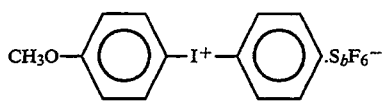

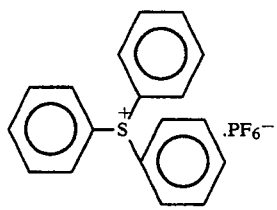

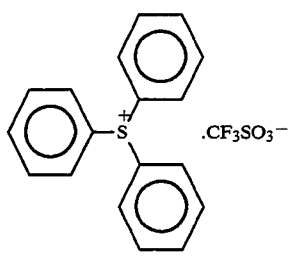

The photo-induced acid precursors usable further include sulfonic acid esters of the N-hydroxyimide compounds represented by the following general formula (IV):

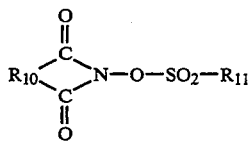

wherein $R_{10}$ represents an optionally substituted arylene, alkylene or alkenylene group and $R_{11}$ represents an optionally substituted alkyl or aryl group; and the esters represented by the following general formula (V):

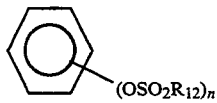

wherein $R_{12}$ represents an optionally substituted alkyl or aryl group and n represents an integer of 1–3.

The arylene group represented by $R_{10}$ in the general formula (IV) includes monocyclic and bicyclic arylene groups, among which phenylene, naphthylene and the like are preferable. As preferable substituents on the arylene group, halogen atom, nitro group, acetylamino group and the like can be referred to.

The alkylene group represented by $R_{10}$ includes straight chain and branched chain alkylene groups, among which those having 1–6 carbon atoms are preferable. Particularly preferable alkylene groups are ethylene group, propylene group and the like. As preferable substituents on the alkylene group, halogen atom, lower alkoxy group, monocyclic aryl groups and the like can be referred to.

The alkenylene group represented by $R_{10}$ includes those having 2–4 carbon atoms, among which vinylidene group and the like are preferable. As preferable substituents on the alkenylene group, monocyclic aryl groups and the like can be referred to.

The alkyl group represented by $R_{11}$ includes straight chain, branched chain and cyclic alkyl groups, among which straight chain alkyl groups having 1–8 carbon atoms are preferable. As preferable substituents on the alkyl group, halogen atom, lower alkoxy group and the like can be referred to.

The aryl group represented by $R_{11}$ includes monocyclic and bicyclic aryl groups, among which monocyclic aryl groups are preferable and phenyl group and the like are particularly preferable. As preferable substituents on the aryl group, lower alkyl groups, lower alkoxy groups and halogen atoms can be referred to.

Preferable examples of the sulfonic acid ester of N-hydroxyimide compound represented by the general formula (IV) include the following:

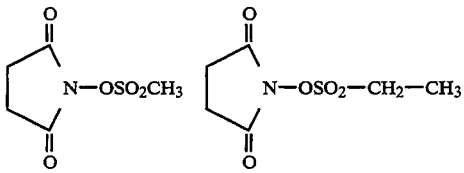

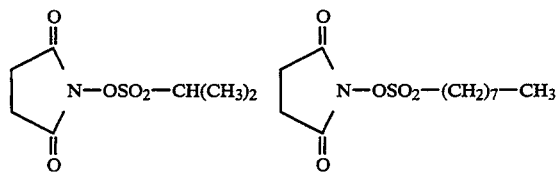

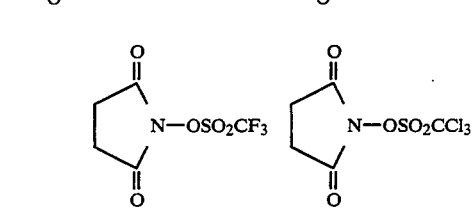

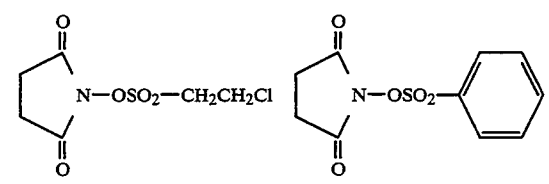

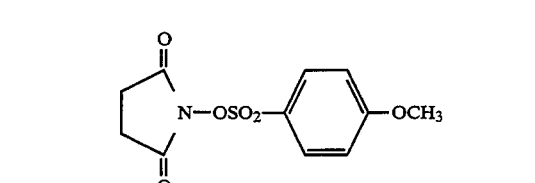

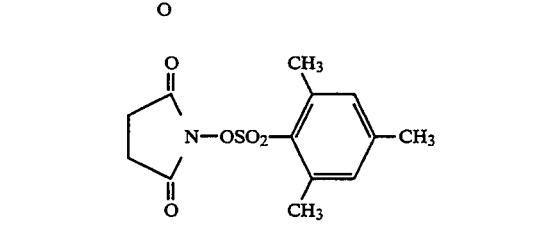

-continued

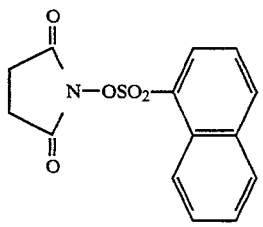

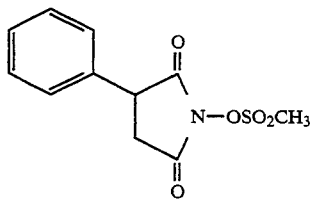

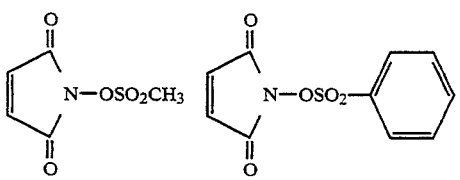

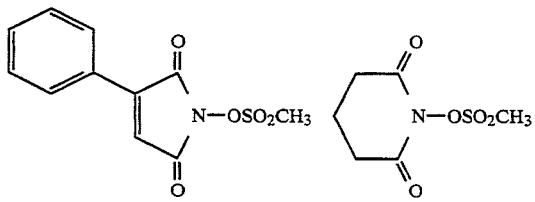

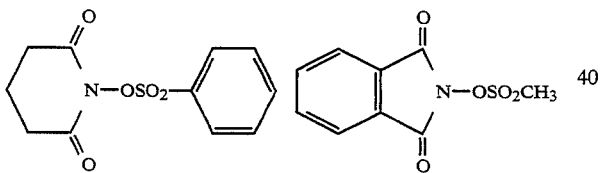

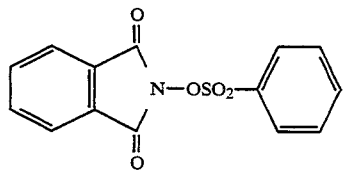

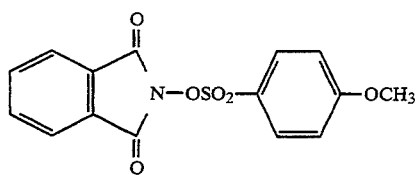

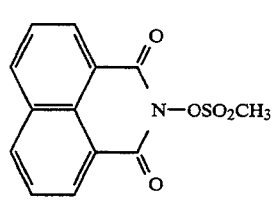

-continued

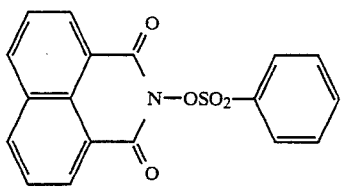

Examples of the ester represented by the general formula (V) include the following:

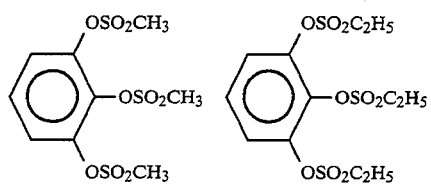

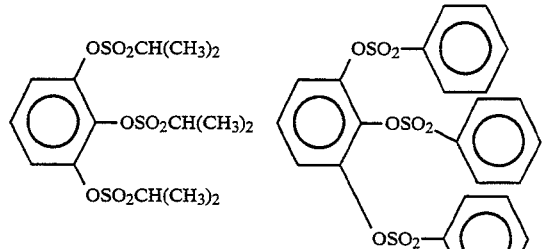

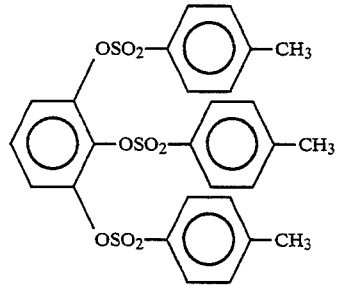

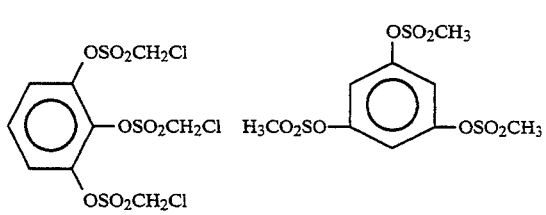

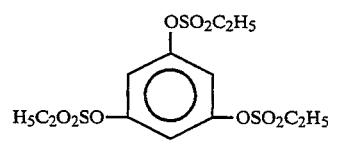

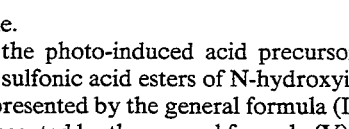

and the like.

Among the photo-induced acid precursors detailed above, the sulfonic acid esters of N-hydroxyimide compounds represented by the general formula (IV) and the esters represented by the general formula (V) are particularly preferable.

The component ratio of the positive photoresist composition of this invention is usually as follows: alkali-soluble resin 20–90% by weight, dissolution inhibitor 5-50% by weight, photo-induced acid precursor 0.1-20% by weight; and preferably as follows: alkali-soluble resin 50-80% by weight, dissolution inhibitor 15-40% by weight, photo-induced acid precursor 1-10% by weight. Into the positive photoresist composition of this invention, various additives conventionally used in this field of the art such as a sensitizer, a dye, an adhesion improver and the like may be added, if desired.

A positive photoresist solution is generally prepared by mixing an alkali-soluble resin, a dissolution inhibitor, a photo-induced acid precursor and the like with a solvent so that concentration of the mixed materials in the resulting positive photoresist solution comes to 1-50% by weight. Examples of the solvent include ethyl cellosolve acetate, methyl cellosolve acetate, ethyl cellosolve, methyl cellosolve, propylene glycol monomethyl ether acetate, propylene glycol monoethyl ether acetate, diethylene glycol dimethyl ether, butyl acetate, ethyl lactate, ethyl pyruvate, methyl isobutyl ketone, 2-heptanone, xylene and the like. These solvents are used either singly or in combination of two or more members.

The cyclic carbonate of this invention is useful as a dissolution inhibitor for a chemically amplified photoresist. The positive photoresist composition of this invention is excellent in performances such as resolution, profile, sensitivity, etc.

Next, this invention will be concretely explained by referring to the following examples.

SYNTHESIS EXAMPLE 1

To a mixture of 100 g (0.37 mole) of the compound represented by the above-mentioned formula (4) (p-OST cyclic dimer, manufactured by Mitsui Toatsu Chemicals, Inc.), 100 g of methyl isobutyl ketone, 13.6 g (0.0074 mole) of 5% aqueous solution of oxalic acid and 30 g (0.37 mole) of acetic acid was dropwise added 30.18 g (0.37 mole) of 37% formalin at 80° C. over a period of one hour. After completing the dropping, the mixture was reacted at 95°-100° C. for 20 hours. The reaction mixture was cooled to 60° C. or below, 100 ml of deionized water was added thereto, and the whole was stirred and then left to stand. After separating the mixture into two liquid layers, the oily layer was several times washed with each 100 ml portion of deionized water, the methyl isobutyl ketone was distilled off, and the residue was mixed into ethyl cellosolve acetate to prepare a resin solution having a solid concentration of 40% (Resin A). The resin thus obtained had a polystyrene-converted weight average molecular weight of 3,975 as measured by GPC.

EXAMPLE 1

To a mixture of 26.8 g (0.1 mole) of the compound represented by the above-mentioned formula (4) (p-OST cyclic dimer manufactured by Mitsui Toatsu Chemicals, Inc.) and 107 g of tetrahydrofuran were added 48.0 g (0.22 mole) of di-t-butyl dicarbonate (manufactured by Wako Pure Chemicals), 36.5 g (0.26 mole) of potassium carbonate and 0.1 g of crown ether (18-crown-6). After the addition, the resulting mixture was stirred at room temperature for 24 hours. After filtering the reaction mixture, the filtrate was concentrated, 300 g of ethyl acetate was added to the residue, and then the solution thus obtained was washed with water. The washed solution was concentrated to obtain a compound represented by the following formula (5):

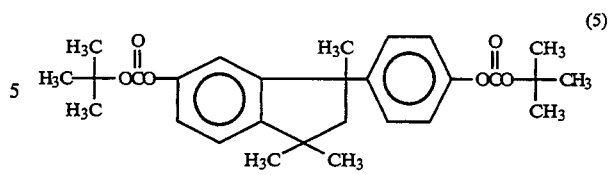

(5)

Elementary analyses of the compound obtained herein were as shown below:

| | | |
|---|---|---|
| Found | C 71.7%, | H 8.0% |
| Calculated | C 71.8%, | H 7.7% |

FIG. 1 illustrates $^1$H-NMR (measured with GX-270 manufactured by Nippon Denshi) of the compound.

Figure 2:
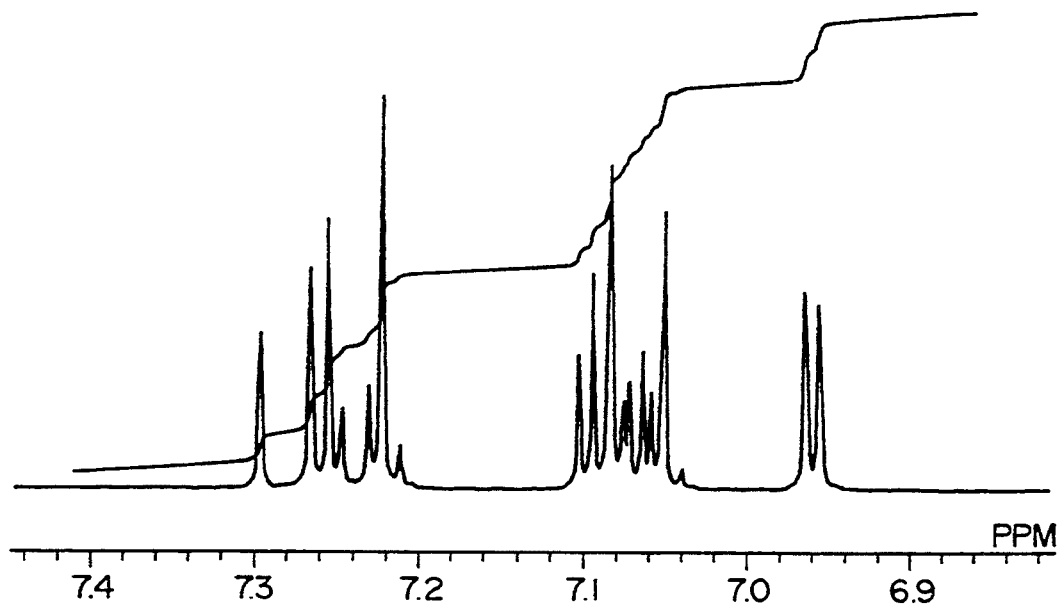
FIG. 2 is an enlarged portion of the spectrum of FIG. 1.

FIG. 2 illustrate enlarged peaks which appeared adjacent to 7 PPM of FIG. 1.

EXAMPLE 2

In 29.7 parts by weight of diethylene glycol dimethyl ether were dissolved 33.8 parts by weight of Resin A obtained in Synthesis Example 1, 3 parts by weight of the compound represented by formula (5) obtained in Example 1 and 1.5 parts by weight of pyrogallol trimesylate. The resulting solution was filtered with a Teflon filter having a pore size of 0.2 μm to prepare a resist solution. A silicon wafer having been washed in the conventional manner was coated with the resist solution by the use of a spin coater. Then, the silicon wafer was pre-baked on a hot plate at 100° C. for one minute to adjust the film thickness to 0.7 μm. Then, the coating film thus formed was exposed to light through a patterned reticle by means of KrF Excimer Laser Stepper (manufactured by Nicon, NRS-1755EX8NA=0.45) having an exposing light wavelength of 245 nm. After the exposure, the wafer was heated on a hot plate at 80° C. for 90 seconds, and thereafter developed with 2.38% (by weight) aqueous solution of tetramethylammonium hydroxide to obtain a positive pattern. Observation of the formed fine pattern by means of an electron microscope revealed that 0.35 μm line-and-space pattern could be resolved with a good profile at a sensitivity of 85 mJ/cm$^2$.

EXAMPLE 3

A positive pattern was prepared by repeating Example 2, except that the pyrogallol trimesylate was replaced with ethanesulfonic triester of pyrogallol. Observation of the formed fine pattern by means of an electron microscope revealed that a 0.35 μm line-and-space pattern could be resolved with a good profile at a sensitivity of 150 mJ/cm$^2$.

EXAMPLE 4

A positive pattern was prepared by repeating Example 2, except that the pyrogallol trimesylate was replaced with benzenesulfonic acid ester of N-hydroxysuccinimide. Observation of the formed fine pattern by means of an electron microscope revealed that a 0.50 μm line-and-space pattern could be resolved with a good profile at a sensitivity of 180 mJ/cm$^2$.

EXAMPLE 5

A positive pattern was prepared by repeating Example 2, except that the pyrogallol trimesylate was replaced with isopropylsulfonic acid ester of N-hydroxysuccinimide. Observation of the formed fine pattern by means of an electron microscope revealed that a 0.70 μm line-and-space pattern could be resolved with a good profile at a sensitivity of 180 mJ/cm².

EXAMPLE 6

In 39.2 parts by weight of ethyl cellosolve acetate were dissolved 53.8 parts by weight of Resin A obtained in Synthesis Example 1, 5 parts by weight of the compound represented by formula (5) obtained in Example 1 and 2.0 parts by weight of α-phenylsulfonylacetophenone. The solution thus obtained was filtered with a Teflon filter having a pore size of 0.2 μm to prepare a resist solution. Then, a silicon wafer having been washed in a conventional manner was coated with the resist solution up to a thickness of 0.7 μm by the use of a spin coater. Then the wafer was pre-baked in an oven at 100° C. for one minute. Then the coating film was exposed to far ultraviolet light through a patterned chromium mask by means of CANON Proximity Mask Aligner PLA-501F provided with CM-250 mirror. After the exposure, the wafer was heated on a hot plate at 120° C. for one minute, and then developed with 2.0% (by weight) aqueous solution of tetramethylammonium hydroxide to obtain a positive pattern. The sensitivity determined from the characteristic curve between an amount of exposure to light and film thickness retention was 40 mJ/cm² (exposure at 254 nm, at a film thickness retention of 0%). Observation of the formed pattern by means of an electron microscope revealed that a 0.8 μm fine pattern was resolved and the profile was good.

EXAMPLE 7

Example 6 was repeated, except that the α-phenylsulfonylacetophenone was replaced with 5.0 parts by weight of diphenyl disulfone. A sensitivity of 12 mJ/cm² (254 nm) was obtained. A 0.8 μm fine pattern was resolved, and the profile was good.

EXAMPLE 8

Example 6 was repeated, except that the Resin A was replaced with 21.52 parts by weight of polyvinylphenol (MARUKA LYNCUR-M, manufactured by Maruzen Sekiyu) and the compound represented by formula (5) was used in an amount of 6 parts by weight. A fine pattern similar to that of Example 6 was obtained. Sensitivity and profile were also good.

EXAMPLE 9

Example 6 was repeated, except that the α-phenylsulfonylacetophenone was replaced with 2.5 parts by weight of an onium salt represented by the following formula (6):

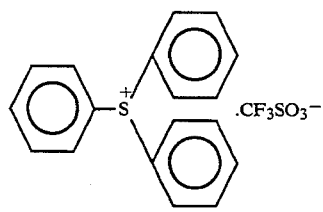

(6)

A fine pattern similar to that of Example 6 was obtained. Sensitivity and profile were also good.

Comparative Example 1

Example 6 was repeated, except that Resin A was replaced with 21.52 parts by weight of polyvinylphenol (MARUKA LYNCUR-M, manufactured by Maruzen Sekiyu), the compound represented by formula (5) was replaced with 5 parts by weight of a compound represented by the following formula (7):

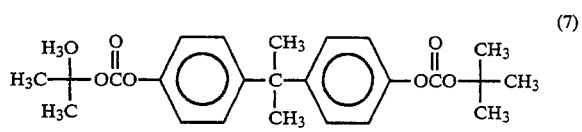

(7)

and the α-phenylsulfonylacetophenone was replaced with 1.2 parts by weight of an onium salt represented by the following formula (8):

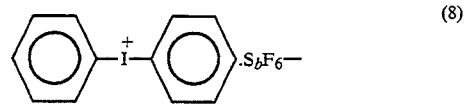

(8)

The sensitivity was 85 mJ/cm² (254 nm), and 0.8 μm pattern could not be formed.

Comparative Example 2

Comparative Example 1 was repeated, except that the polyvinylphenol (MARUKA LYNCUR-M, manufactured by Maruzen Sekiyu) was replaced with a modified product of said resin wherein ¼, by number, of the total phenolic —OH groups had been converted to —OC(O)O—C(CH₃)₃ groups. As the result, scum was noticeable after development, even although 0.8 μm pattern could be resolved.

What is claimed is:
1. A positive photoresist composition comprising:
a cyclic carbonate compound represented by general formula (I):

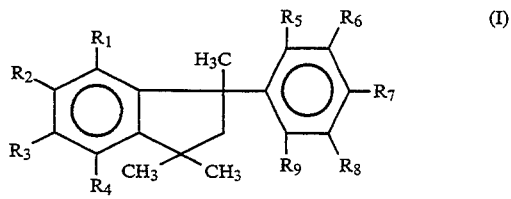

(I)

wherein $R_1$ to $R_9$ independently of one another each represent a hydrogen atom, a halogen atom, an optionally substituted straight chain or branched chain alkyl or alkenyl group, a t-butoxycarbonyloxy group or an acetyl group; provided that at least one of $R_1$ to $R_4$ is a t-butoxycarbonyloxy group and at least one of $R_5$ to $R_9$ is a t-butoxycarbonyloxy group;
an alkali-soluble resin; and
a photo-induced acid precursor.

2. A positive photoresist composition according to claim 1, wherein said alkali-soluble resin is polyvinylphenol, or a novolac resin which is obtained through a condensation reaction of
a phenol compound represented by the following general formula (III):

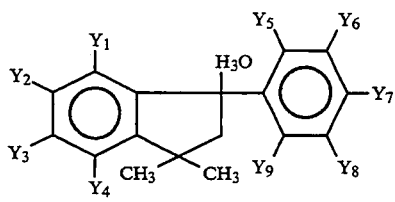

(III)

wherein $Y_1$ to $Y_9$ independently of one another each represent a hydrogen atom, a halogen atom, an optionally substituted straight chain or branched chain alkyl or alkenyl group, an —OH group or an acetyl group, provided that at least one of $Y_1$ to $Y_9$ is an —OH group and at least two hydrogen atoms are attached to the ortho- or para-position of said —OH group, and
an aldehyde.

3. A positive photoresist composition according to claim 2, wherein said photo-induced acid precursor is sulfonic acid ester of a N-hydroxyimide compound represented by the following general formula (IV):

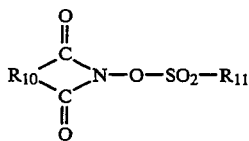

(IV)

wherein $R_{10}$ represents an optionally substituted arylene, alkylene or alkenylene group and $R_{11}$ represents an optionally substituted alkyl or aryl group.

4. A positive photoresist composition according to claim 1 or 2, wherein said photo-induced acid precursor is an ester represented by the following general formula (V):

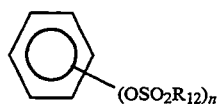

(V)

wherein $R_{12}$ represents an optionally substituted alkyl or aryl group and n represents an integer of 1–3.

5. A positive photoresist composition according to claim 2, wherein the compound (III) is a compound in which at least one of $Y_1$ to $Y_4$ is —OH group, and at least one of $Y_5$ to $Y_9$ is —OH group.

6. A positive photoresist composition according to claim 5, wherein said photo-induced acid precursor is sulfonic acid ester of a N-hydroxyimide compound represented by the following general formula (IV):

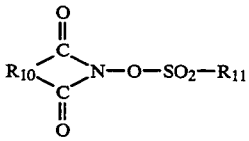

(IV)

wherein $R_{10}$ represents an optionally substituted arylene, alkylene or alkenylene group and $R_{11}$ represents an optionally substituted alkyl or aryl group.

7. A positive photoresist composition according to claim 5, wherein said photo-induced acid precursor is an ester represented by the following general formula (V):

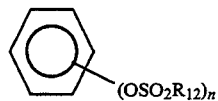

(V)

wherein $R_{12}$ represents an optionally substituted alkyl or aryl group and n represents an integer of 1, 2 or 3.

8. A positive photoresist composition according to claim 1, wherein $R_1$ to $R_9$ independently of one another each represent a hydrogen atom, a halogen atom, an optionally substituted straight chain or branched chain $C_1$–$C_5$ alkyl or $C_2$–$C_5$ alkenyl group, a t-butoxycarbonyloxy group or an acetyl group.

9. A positive photoresist composition according to claim 8, wherein said alkyl or alkenyl group is substituted with a substituent selected from the group consisting of a halogen atom, an hydroxy group, a —SH group, and a phenyl group.

10. A positive photoresist composition according to claim 1, wherein $R_1$ to $R_9$ independently of one another each represent a hydrogen atom or an alkyl group, provided that at least one of $R_1$ to $R_4$ is a t-butoxycarbonyloxy group and at least one of $R_5$ to $R_9$ is a t-butoxycarbonyloxy group.

11. A positive photoresist composition according to claim 10, wherein $R_1$ to $R_9$ independently of one another each represent a hydrogen atom, methyl group or ethyl group, provided that at least one of $R_1$ to $R_4$ is a t-butoxycarbonyloxy group and at least one of $R_5$ to $R_9$ is a t-butoxycarbonyloxy group.

12. A positive photoresist composition according to claim 1, wherein said cyclic carbonate compound is:

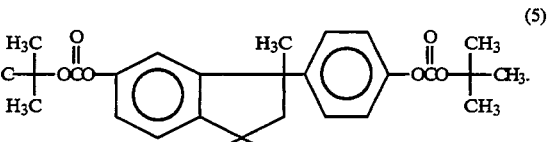

(5)

13. A positive photoresist composition according to claim 1, wherein said cyclic carbonate compound is present in an amount of 5–50% by weight, said alkali-soluble resin is present in an amount of 20–90% by weight, and said photo-induced acid precursor is present in the amount 0.1–20% by weight.

14. A positive photoresist composition according to claim 1, wherein said cyclic carbonate compound is present in an amount of 15–40% by weight, said alkali-soluble resin is present in an amount of 50–80% by weight, and said photo-induced acid precursor is present in the amount of 1–10% by weight.

* * * * *